United States Patent
Ou (12)

(10) Patent No.: US 10,874,773 B2
(45) Date of Patent: Dec. 29, 2020

(54) TWO-STEP BATCH PROCESS FOR COATING SURGICAL NEEDLES

(71) Applicant: Ethicon, Inc., Somerville, NJ (US)

(72) Inventor: Duan Li Ou, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 347 days.

(21) Appl. No.: 14/311,964

(22) Filed: Jun. 23, 2014

(65) Prior Publication Data

US 2015/0367039 A1 Dec. 24, 2015

(51) Int. Cl.
| | | |
|---|---|---|
| *A61L 31/10* | (2006.01) |
| *B05D 1/18* | (2006.01) |
| *B05D 5/08* | (2006.01) |
| *B05D 7/24* | (2006.01) |
| *B05D 7/14* | (2006.01) |
| *A61B 17/06* | (2006.01) |
| *C09D 183/04* | (2006.01) |
| *C08L 83/04* | (2006.01) |
| *A61B 17/00* | (2006.01) |
| *C08G 77/20* | (2006.01) |

(52) U.S. Cl.
CPC ........ *A61L 31/10* (2013.01); *A61B 17/06066* (2013.01); *A61B 17/06109* (2013.01); *B05D 1/18* (2013.01); *B05D 5/08* (2013.01); *B05D 7/14* (2013.01); *B05D 7/24* (2013.01); *C08L 83/04* (2013.01); *C09D 183/04* (2013.01); *A61B 2017/00526* (2013.01); *A61B 2017/0608* (2013.01); *A61L 2420/02* (2013.01); *C08G 77/20* (2013.01)

(58) Field of Classification Search
CPC .............................. B32B 17/06; A61B 17/00
USPC .......................................... 428/429; 606/223
See application file for complete search history.

(56) References Cited

U.S. PATENT DOCUMENTS

| | | | |
|---|---|---|---|
| 3,775,452 A | 11/1973 | Karstedt | |
| 5,181,416 A | 1/1993 | Evans | |
| 5,258,013 A * | 11/1993 | Granger | ........... A61B 17/06066 427/372.2 |
| 5,630,268 A | 5/1997 | Smith et al. | |
| 5,644,834 A | 7/1997 | Smith et al. | |
| 5,661,893 A | 9/1997 | Smith et al. | |
| 5,701,656 A | 12/1997 | Smith et al. | |
| 5,776,268 A | 7/1998 | McJames et al. | |
| 5,913,875 A | 6/1999 | Smith et al. | |
| 6,018,860 A | 2/2000 | Smith et al. | |
| 6,252,195 B1 | 6/2001 | Mosavi et al. | |
| 7,041,088 B2 | 5/2006 | Nawrocki et al. | |
| 2003/0114882 A1 | 6/2003 | Roby | |

(Continued)

OTHER PUBLICATIONS

Pavlovich, L. J. et al. "A Synthetic Membrane for Testing Needle Penetration". *Journal of Applied Biomaterials* 1993; 4: 157-160, John Wiley & Sons, Inc.

(Continued)

*Primary Examiner* — Dah-Wei D. Yuan
*Assistant Examiner* — Andrew J Bowman

(57) ABSTRACT

A novel two-step process for batch coating surgical needles with cross-linked silicone coatings is disclosed. The surgical needles are cured using a two-step process. The coatings on the needles are partially cured in the first step and mechanically separated. The coatings on the needles are then fully cured in the second step.

13 Claims, 8 Drawing Sheets

(56) References Cited

U.S. PATENT DOCUMENTS

2013/0122314 A1* 5/2013 Ou ........................ A61L 29/085
    428/429

OTHER PUBLICATIONS

Disclosed anonymously, "Methods for coating surgical suture needles", Research Disclosure, Mason Publications, Hampshire, GB, vol. 503, No. 68, Mar. 1, 2006 XP007136039, ISSN: 0374-4353.

* cited by examiner

TWO-STEP BATCH PROCESS FOR COATING SURGICAL NEEDLES

FIELD OF THE INVENTION

The field of art to which this invention relates is surgical needles, more particularly lubricious coatings for surgical needles and methods for applying such coatings.

BACKGROUND OF THE INVENTION

Surgical needles and surgical sutures are widely used medical devices in the medical arts. Typically, the surgical sutures are pre-mounted to the proximal ends of the surgical needles by the manufacturers. Surgical sutures are used in most surgical procedures for a variety of functions including tissue repair and approximation, securement of medical devices to tissue including mesh implants, artificial heart valves, artificial blood vessels, etc., vessel anastomosis and attachment, bone repair, tissue anchoring, etc. In order to have maximum utility to the surgeon during a surgical procedure, it is necessary that the surgical needle be capable of easily and smoothly penetrating and moving through tissue for multiple passes with minimal and substantially constant force. The amount of force necessary to move a surgical needle through tissue with minimal trauma to the tissue will depend in part on the type of tissue to be penetrated. Needle designs having a variety of geometries are available for use with different types of tissue to provide the desired tissue penetration qualities including taper point needles, blunt tip needles, and cutting edge needles. The wire size of the needle will also affect the force to penetrate. In order to assist needle performance, it is known to apply lubricious coatings to surgical needles to improve their penetration and movement through tissue. Lubricious coatings are conventionally applied and required for implantable or insertable medical devices such as hypodermic needles, surgical needles, and cutting equipment with cutting edges such as knives, scalpels, scissors and blades with cutting edges that contact tissue. The primary purpose of such coatings is to reduce the penetration force and ease the insertion of the device into and through tissue as the needle forms a passageway through tissue for the surgical suture.

Most conventional lubricious coatings used for medical devices such as surgical needles are silicone polymer based. Examples of such silicone materials include the polyalkylsiloxanes. The preferred polyalkylsiloxanes conventionally used are polydimethylsiloxanes. The lubricious silicone coatings may be applied to surgical needles using conventional coating processes known in this art, including dip coating and spraying. Examples of silicone coating compositions and coating processes are contained in the following patent applications and patent which are incorporated by reference: U.S. patent application Ser. Nos. 12/858,489; 12/858,485; 12/858,481; 10/034,636; 10/678,560; 13/162,837 and 12/642,373, and U.S. Pat. No. 7,041,088

Surgical needles are commonly manufactured using high speed production processes. The production processes typically utilize high speed inline manufacturing lines. Surgical needle blanks are typically mounted to metal carrier strips and moved through the various sequential manufacturing operations, where they are formed in a step-wise process into surgical needles. The manufacturing process steps may include needle point formation, bending, curving, insertion of body flats, heat treatment, and borehole drilling. In addition, the finished needles may be coated with silicone coatings, e.g., dip coated in silicone coating baths, and moved to drying and curing ovens while on the metal carrier strips. Examples of high speed needle manufacturing processes and equipment are disclosed in the following patents which are incorporated by reference: U.S. Pat. Nos. 5,630,268, 5,644,834, 5,661,893, 5,701,656, 5,776,268, 5,913,875, 6,018,860, and 6,252,195.

Batch silicone coating processes are conventionally used for general line needles, which are typically manufactured in high volumes. For such needles, it is not economical to coat the needles by mounting the needles to a strip that is run through a silicone coating tank. Instead, these needles are conventionally coated in bulk by placing a batch of manufactured surgical needles in baskets or other porous vessels, which are then immersed in a silicone coating bath. The baskets (or porous vessels) are then removed from the bath after a sufficiently effective residence time, and the wet, coated needles are transferred from the baskets to drying/curing trays by dumping or emptying the contents of the baskets out onto the tray surfaces. The needles are typically not singulated, but are cured in a pile as deposited onto the tray surfaces.

Lubricious coatings on most surgical needles are typically applied by conventional batch dip coating processes, in which the needles are first immersed into a silicone solution, and then drained and exposed to a thermal cycle to remove the solvent and cure the silicone polymer. Other conventional coating processes such as spraying or brushing are also utilized. Such batch processes are in contrast to high speed automated production processes where surgical needles are coated while mounted (in a singular fashion) to a carrier strip in a semi-continuous manner when employing a dip coating process, wherein a section of the strip is immersed in a tank of the coating solution and then moved out to a blow off device that is used on-line to remove the excess silicone solution prior to a thermal curing step.

Although conventional batch silicone coating processes are typically effective for their intended purpose, and produce coatings on surgical needles that comply with requirements, there may be some deficiencies associated with their use. First of all, conventional batch dip coating processes use conventional lubricious coatings. Conventional silicone coatings have substantially long cure times and coated needles must be moved to a curing oven while the coating is still wet. The wet coating is susceptible to damage and to being contaminated by dust and dirt particles in the environment, potentially compromising the integrity and performance of the coating. In addition, the wet coatings have a tendency to wick, shrink or move away from the distal end and distal piercing point of the needle, potentially reducing the thickness of the coating to unacceptably low levels thereby potentially affecting penetration performance. Quick or rapid cure coatings have been developed which overcome some of these problems, such as the cross-linkable coating disclosed in published U.S. Pat. App. No. 2013/0122314. Furthermore, needles cured in a batch process are often in contact with other needles during the curing process. After curing, the coated needles may be stuck together at the coating contact points. Separating the needles (e.g., manually) will often remove a section of coating from needles at the contacting attachment points. The performance of such needles through tissue may be adversely affected. This problem particularly presents itself with quick or rapid cure silicone coatings.

Accordingly, there is a need in this art for novel batch coating processes for coating surgical needles with lubricious coatings that provide for improved coating application and coating characteristics.

SUMMARY OF THE INVENTION

Novel batch silicone coating processes for surgical needles are disclosed. A plurality of surgical needles is provided. Preferably, the needles are contained within a porous containment vessel, wherein at least some of the needles are in contact with each other. The vessel and the needles are immersed in a bath containing a silicone coating solution which comprises platinum catalyst and silicone compounds rapidly curable by cross-linking. The containment vessel and needles are removed from the bath. The coatings on the needles are partially cured at a first temperature for a sufficient time such that there is weak needle-to-needle adhesion. The needles are then mechanically separated. The coatings on the needles are then cured at a second temperature for a sufficient time to fully cure the coatings, the second temperature being higher than the first temperature.

Another aspect of the present invention is a method of batch coating a plurality of surgical needles with a cross-linked, platinum catalyzed lubricious coating. A plurality of surgical needles is provided. A silicone coating solution is applied to the plurality of needles. The silicone coating solution includes a platinum catalyst and a silicone compound curable by cross-linking to provide a coating on each needle. The coatings on the needles are partially cured at a first temperature for a sufficient time such that there is weak needle-to-needle adhesion. The needles are then mechanically separated and the coatings on the needles are fully cured at a second temperature for a sufficient time, the second temperature being higher than the first temperature.

These and other aspects and advantages of the present invention will become more apparent from the following description and accompanying drawings.

DETAILED DESCRIPTION OF THE INVENTION

Figure 1:
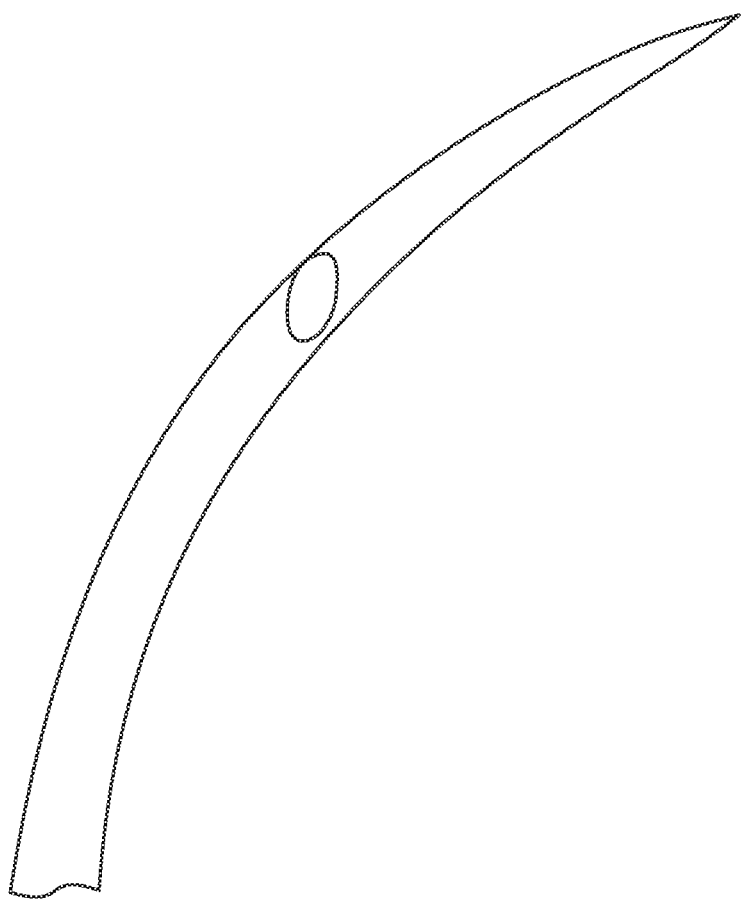
FIG. 1 is a photograph of a damaged cross-linked silicone coating on a surgical needle produced in a conventional one-step curing batch coating process.

The terms silicone and siloxane are conventionally used interchangeably in this art, and that usage has been adopted herein.

The present invention is directed to novel processes for applying lubricious silicone coating compositions, which are particularly useful for coating surfaces of medical devices, such as surgical needles and other tissue piercing or tissue cutting devices. The coating compositions include a mixture of a cross-linkable siloxane polymer and a non-cross-linkable siloxane polymer, a conventional silicone cross-linking agent, and a platinum catalyst. The silicone polymer components are blended with conventional aromatic organic solvents, including, for example, xylene and aliphatic organic solvents (such as, for example, hexane or its commercial derivatives) to form coating solutions or compositions. Particularly preferred coating compositions useful in the novel processes of the present invention are disclosed in copending, commonly-assigned U.S. patent application Ser. No. 13/296,771 which is incorporated by reference. The coatings of present invention are conventionally referred to as crosslinkable, platinum catalyst rapid or command-cure coatings. Rapid or command-cure refers to the time of curing at preferred curing temperature of about 10 sec to about 60 sec at an exemplary temperature 160° C. These coatings are different from the commonly used condensation cure coatings which do not utilize platinum catalysts, and are curable much more slowley, such as for example curable in 1 hour, or typically longer, such as 8 or more hours. In a batch process as practiced herein, as will be appreciated to these skilled in the art, heat transfer through the large batch of needles requires additional time for thermal treatment, to achieve uniformity and thermal equilibrium throughout the entire batch.

The cross-linkable siloxane polymers useful in the coating compositions useful in the processes of the present invention will have reactive functionalities or terminal functional groups, including but not limited to vinyl-terminated, hydroxyl and acrylate functional groups. An example of a hydroxyl functional, cross-linkable siloxane polymer is hydroxyl terminated polydimethylsiloxane, supplied by Nusil Technology, Caprenteria, Calif. under the trade name of MED4162. The cross-linkable siloxane polymers that can be used in the lubricious coatings of the present invention preferably include vinyl-terminated polydialkylsiloxane or vinyl-terminated polyalkoarylsiloxane. Examples include, but are not limited to, the following vinyl-terminated siloxane polymers: polydimethyl siloxane, polydiphenylsilane-dimethylsiloxane copolymer, polyphenylmethylsiloxane, polyfluoropropylmethyl-dimethylsiloxane copolymer and polydiethylsiloxane. It is particularly preferred to use vinyl-terminated cross-linkable polymethyl siloxane.

The non-cross-linkable siloxanes that can be used in the practice of the present invention include polydimethyl siloxane, polyalkylmethylsiloxane, such as polydiethylsiloxane, polyfluoropropylmethylsiloxane, polyoctylmethylsiloxane, polytetradecylmethylsiloxane, polyoctadecylmethylsiloxane, and polyalkylmethyl dimethylsiloxane, such as polyhexadecymethylsiloxane-dimethyl siloxane. It is particularly preferred to use non-cross-linkable polymethylsiloxanes with weight average molecular weights (Mw) greater than 200,000, preferably about 200,000 to about 1,000,000, which are in the form of non-flowable gum having a viscosity greater than 600,000 cps.

The cross-linking agents that can be used in coatings applied by the novel processes of the present invention include conventional silicone cross-linking agents such as, for example, polymethylhydrosiloxane, polymethylhydro-co-polydimethylsiloxane, polyethyhydrosiloxane, polymethylhydrosiloxane-co-octylmethylsiloxane, polymethylhydrosiloxane-co-methylphenylsiloxane. One preferred conventional cross-linking agent for use in the coatings applied by the novel processes of the present invention is polymethylhydrosiloxane. Precise control of cross-link density in the coatings of the present invention is achieved by precise control of the ratio of non-cross-linkable silicone polymer (e.g., polydimethylsiloxane) to fully cross-linked polymer. The fully cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. The ratio between non-cross-linkable polymer, e.g., polydimethylsiloxane, and fully cross-linked polymer is sufficiently effective to provide structural reinforcement to the resulting interpenetrating polymer networks, and is typically between about 0.1 wt./wt. and about 9 wt./wt., preferably between about 0.43 wt./wt. and about 2.33 wt./wt. The vinyl-terminated cross-linkable base polymer, e.g., polydimethylsiloxane base polymer, useful in the coatings applied by the processes of the present invention will typically have a weight average molecular weight (Mw) of between about 10,000 and about 500,000 and preferably between about 50,000 to about 250,000. Examples of such a polymer include, but are not limited to: Gelest Product Code No. DMS-V51, DMS-V52, DMS-V61, DMS-V71, etc., available from Gelest, Inc., Morrisville, Pa. 19067.

The cross-linkable siloxane polymer is believed to form the matrix phase of the coating on a surface or surfaces of a medical device. Vinyl-terminated polydimethylsiloxane reacts with polymethylhydrosiloxane cross-linker in the presence of platinum catalyst under appropriate conditions; the vinyl-terminated polydimethylsiloxane linear polymers are fully cross-linked to each other as the result of this reaction. The amount of polymethylhydrosiloxane cross-linker is in large stoichiometric excess compared to the vinyl-terminated polydimethylsiloxane base polymer. It is believed that the extra SiH functional groups in the cross-linker react with the OH functional groups on the surface of the oxide layer of the medical devices, e.g., stainless steel needles, to form Si—O—Fe bonds at elevated temperature. Covalent bonds thus created between the silicone coating and the device or needle surface, as the result of this reaction, result in the adhesive attachment of the coating to the metallic surface. Attachment to a polymeric surface is believed to occur in the following manner: the OH and COOH functions on the surface of a polymeric surface react with SiH functions in the silicone coating to from Si—O—C bonds at elevated temperature.

The polymethyhydrosiloxane cross-linkers, or cross-linking agents, used in the practice of the present invention will typically have a weight average molecular weight (Mw) between about 1000 and about 3000, and preferably between about 1400 and about 2100. An example of this polymer cross-linker includes, but is not limited to, Gelest Product Code No. HMS-991, HMS-992, available from Gelest, Inc., Morrisville, Pa. 19607.

Polymethylhydro-co-polydimethylsiloxane can also be used as a cross-linker or cross-linking agent in the coatings applied by the novel processes of the present invention. Examples of this polymer include, but are not limited to, Gelest Product Code No. HMS-301, HMS-501. The weight average molecular weight of such siloxane polymer cross-linking agents will typically be between about 900 and about 5,000, and preferably about 1,200 to about 3,000.

The non-cross-linkable siloxane polymer that may be used in the lubricious coatings applied by the processes of the present invention is preferably trimethylsilyl-terminated polydimethylsiloxane; which is a linear high molecular weight polydimethylsiloxane polymer, that does not contain reactive functional groups. This polymer provides a non-cross-linked phase in the resulting silicone coating, and is believed to disperse in the matrix phase made from the cross-linked cross-linkable siloxane. The weight average molecular weight of non-cross-linkable siloxane polymer will typically be greater than about 200,000, preferably between about 200,000 to about 10,000,000, and more preferably between about 400,000 to about 700,000. Examples of this polymer include, but are not limited to, Gelest Product Code No. DMS-D-56, DMS-T62, DMS-T61, DMS-D72.

Conventional catalysts may be used in the coatings useful in the practice of the present invention. The catalysts include platinum and platinum compounds, such as Ashby catalyst and other known to these skilled in the art. One example of a highly active platinum catalyst (the "Karstedt catalyst") is disclosed in U.S. Pat. No. 3,775,452, which is incorporated by reference. Vinyl-terminated polydimethylsiloxane can react with a polymethylhydrosiloxane cross-linker in less than one minute at ambient temperature with as little as 10 ppm of the Karstedt catalyst. Novel, fast-curing platinum catalysts have been developed to improve upon the characteristics of the Karstedt catalyst and other catalysts. An example of such a catalyst is a catalyst prepared by reacting the Karstedt catalyst with ethynylcyclohexanol (as disclosed in U.S. patent application Ser. No. 13/296,771). Such a catalyst provides greater control over curing of silicone coating solutions. This is conventionally referred to as "command cure".

The formula of the resulting platinum complex catalyst (platinum ivinyltetramethyldisiloxane ethynylcyclohexanol complex) is:

$$Pt[(CH_2=CH)(Me)_2Si]_2O \cdot C_6H_{10}(OH)(C \equiv CH)$$

Such a preferred command cure catalyst is inhibited at low or ambient temperatures and activated at higher or curing temperatures; that is, the catalyst is inactivated at lower or ambient temperatures and activated at higher or curing temperatures. This allows for command cure (command cure catalytic action) of the cross-linkable components in silicone coatings to rapidly form coating films at desired curing temperatures, and provides for long pot life.

The silicone coating solutions that are used in the coating processes of the present invention to coat surgical needles may be prepared in the following manner. The above-described silicone polymers and platinum catalysts, including the novel platinum complex catalyst, are dispersed into organic solvents to form the novel lubricious coating solutions or compositions of the present invention. Both aromatic and aliphatic solvents can be used for the silicone dispersions, however, aromatic solvents are most commonly used for silicone dispersions. Typical examples of useful aromatic solvents include, but are not limited to, xylene and toluene. Aliphatic solvents which are useful include, but are not limited to, pentane, heptanes, hexane and their mixtures. An example of an aliphatic solvent mixture is Exxon Isopar K® solvent. The organic solvents are added at a concentration sufficient to provide effective blending of the silicone polymer components into a homogeneous coating solution that may effectively applied by conventional coating process equipment. The total solvent concentration sufficient to be effective is typically between about 75 wt. % to about 99.5 wt. %, and is more typically between about 85 wt. % to about 98.5 wt. %, depending upon the coating thickness requirement. Those skilled in the art will appreciate that the coating thickness can be engineered by changing the solids content of the coating solution.

The following production procedure as described utilizes conventional mixing equipment in typical and conventional production facilities. The coating compositions useful in practice of the processes of the present invention may be preferably prepared in the following manner. Initially, a suitable organic solvent such as xylene is added to a conventional mixing vessel together with a suitable platinum catalyst and mixed for a sufficiently effective time, for example, up to about 10 minutes, to form a solution. Then, a suitable non-cross-linkable silicone polymer component, such as trimethylsilyl-terminated polydimethylsiloxane, and a suitable vinyl-terminated cross-linkable silicone polymer component, such as polydimethylsiloxane, are dispersed into the solution for a sufficiently effective time; for example, for up to about two hours until fully homogeneous. A suitable organic solvent such as Isopar K® solvent is then added to the solution, and the solution is further mixed for a sufficiently effective time, for example, for about one hour, prior to the addition of a suitable cross-linking agent such as polymethylhydrosiloxane cross-linker. Then, the cross-linking agent is added to the solution and the solution is fully blended for a sufficiently effective time. The length of such time can be, for example, one additional hour after all of the components have been added to the mixing vessel.

Other conventional blending and mixing processes and equipment may be used to manufacture the novel silicone coating compositions of the present invention. For example, the sequence can be modified to some extent when using various other suitably effective conventional mixing equipment, such as a double planetary mixer. All of the components may be mixed in one step in such equipment.

Although not necessarily preferred, in order to reduce VOC emissions, it is possible to formulate the lubricious silicone coating compositions in a less volatile organic solvent, an aqueous/organic solvent mixture, or an aqueous solvent solution. This can be done by done in a conventional manner similar to that used for conventional low VOC or water-based polymeric coatings.

In the following paragraph the wt. % is the wt. % of total solid content in the coating solution. The coating compositions useful in the coating processes of the present invention will contain sufficient amounts of the polymeric components, cross-linking agent, catalyst, and solvent to effectively provide a silicone coating having high lubricity and durability, a long pot life, and be suitable for application in conventional coating processes using conventional coating equipment. Typically, the amount of the non-cross-linkable silicone polymer will be about 10 wt. % to about 90 wt. % (total solids), more typically about 30 wt. % to about 70 wt. % (total solids), and preferably about 40 wt. % to about 60 wt. % (total solids). The amount of the cross-linkable silicone polymer will typically be about 10 wt. % to about 90 wt. % (total solids), more typically about 30 wt. % to about 70 wt. % (total solids), and preferably about 40 wt. % to about 60 wt. % (total solids). The amount of the silicone cross-linking agent will typically be about 0.2 wt. % to about 1.8 wt. % (total solids), more typically about 0.6 wt. % to about 1.4 wt. % (total solids), and preferably about 0.8 wt. % to about 1.2 wt. % (total solids). The amount of the platinum catalyst based upon the total solids in the lubricious silicone coating compositions (platinum element in total solids) will typically be about 0.0004 wt. % to about 0.0036 wt. %, more typically about 0.0012 wt. % to about 0.0028 wt. %, and preferably about 0.0016 wt. % to about 0.0024 wt. %.

The amount of organic solvent in the coating compositions useful in the novel coating processes of the present invention will typically be about 75 wt. % to about 99.5 wt. %, more typically about 28 wt. % to about 99 wt. %, and preferably about 15 wt. % to about 98.5 wt. %. Those skilled in the art will appreciate that the amount of solvent present in the coating compositions will vary with several factors, and that the solvent quantity in the coating compositions will be selected to engineer an efficacious coating. The factors typically considered include the method of application, the method of cure, the coating equipment utilized, ambient conditions, thickness, etc. It will be appreciated that each of the components of the coating compositions of the present invention may consist of blends of those components. For example, two or more different molecular weight non-cross-linkable silicone polymers may be used, or two or more cross-linkable silicone polymers having different functionalities and/or molecular weights may be used, etc.

The silicone lubricious coating compositions used in the processes of the present invention may be applied to one or more surfaces of a medical device, such as a surgical needle, using conventional coating techniques and processes and conventional coating equipment. An example of coating equipment that can be used to apply the coatings includes, but is not limited to, conventional dip coating tanks and conventional ovens for curing. The coating compositions can also be applied by conventional brushing, rolling, or spraying processes, and any equivalent processes, and may be cured as well by any equivalent curing methods.

The novel coating processes of the present invention have particular applicability for applying silicone coatings to surgical needles in batch processes. In a conventional batch silicone coating process, uncoated surgical needles are placed in bulk in a porous basket or vessel. The porous basket or vessel is then immersed in a coating bath containing the desired silicone coating solution. After immersion for a sufficient period of time, the basket and the needles are removed from the coating bath, and excess coating solution is allowed to drip off of the coated needles. The coated needles are then optionally air dried and placed on a conventional curing tray prior to moving them to a thermal curing oven. After thermally curing the needles in the conventional process, it is known that needles can stick together at various contact points requiring mechanical separation and possible disruption of the silicone coatings and an associated possible decrease in needle performance.

Figure 7:
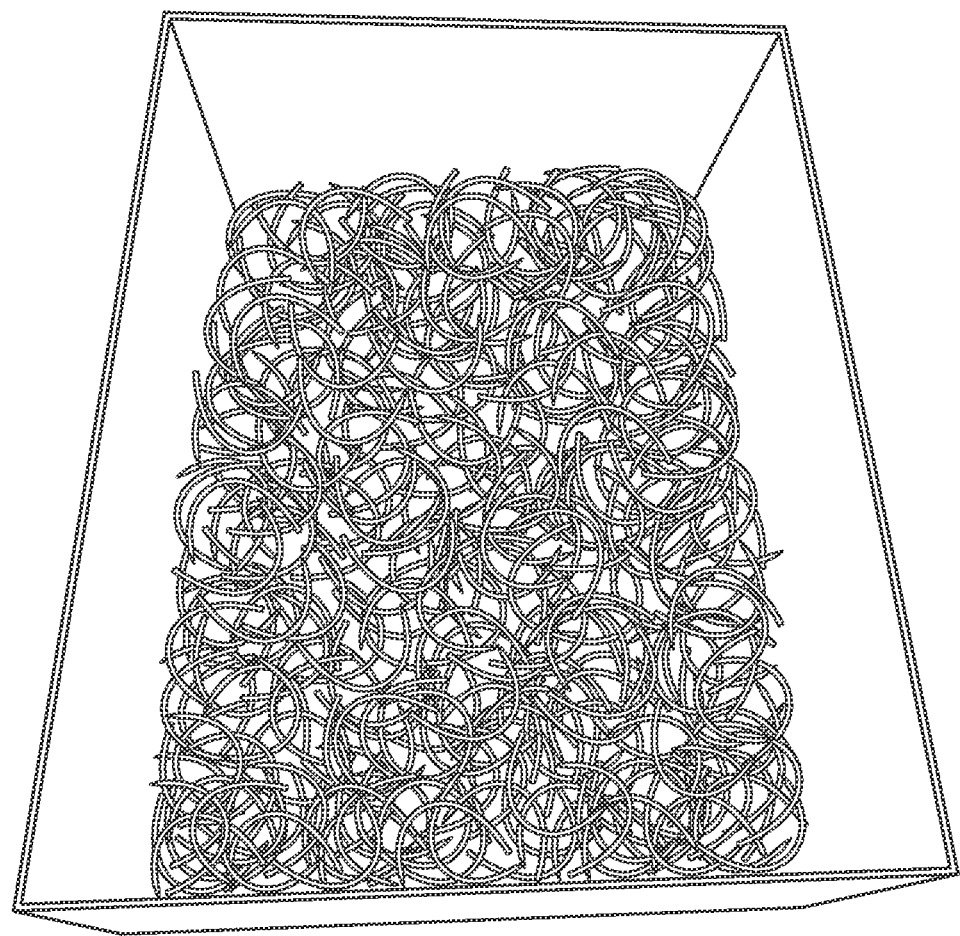
FIG. 7 is an illustration of a batch of needles in a conventional porous basket used in a batch silicone coating process prior to immersing the basket and the needles in a silicone coating bath.
Figure 8:
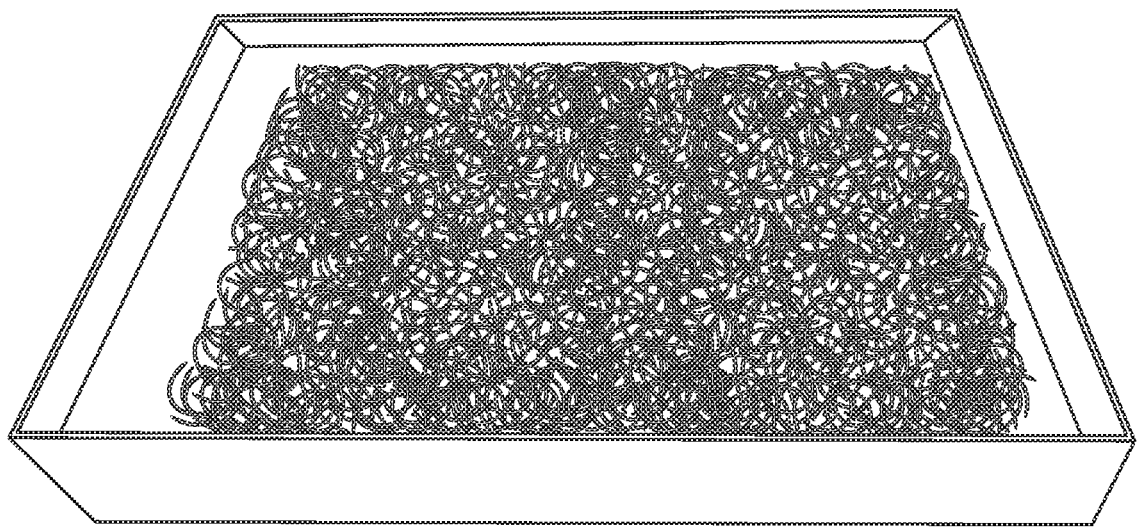
FIG. 8 is an illustration of a batch needles after batch silicone coatings have been applied in a dip tank, and spread out on a conventional drying tray prior to curing.

In the novel batch silicone coating processes of the present invention, the medical devices, such as surgical needles, are preferably placed in bulk in a porous or perforated basket or containment vessel that allows fluid flow through the basket or vessel. An example of a conventional basket is seen in FIG. 7. The basket or containment vessel is then immersed into a suitable silicone coating bath containing a silicone coating solution as described above. The coating bath solution is preferably maintained at ambient temperature. The needles will be maintained in the coating bath for a sufficient period of time to provide an effective coating on the needles. Typically, the immersion time will be about 1 second to about 1 hour, more typically about 3 seconds to about 5 minutes, and preferably about 5 seconds to about 10 seconds. The needles are removed from the coating bath and excess coating may be allowed to drip off. The needles having a wet, uncured silicone coating are then transferred to a curing tray. An example of a conventional curing tray to which coated needles have been transferred is seen in FIG. 8; many of the needles are seen to be in contact with other needles. The curing tray is placed in a conventional thermal curing oven for a sufficiently effective period of time at a sufficiently effective temperature to partially cure the coatings. The term "partially cure" is defined to mean that the silicone coating is partially cross-linked and has a strength that is substantially lower than the strength of the fully-cured coating, allowing the partially-cured needles to be easily mechanically separated from each other, for example manual separation. Typically, the partial cure time will be about 10 minutes to about 8 hours, more typically about 30 minutes to about 4 hours, and preferably about 1 hour to about 2 hours. Typically, the partial cure temperature is maintained at about 80° C. to about 120° C., more typically about 85° C. to about 110° C., and preferably about 90° C. to about 100° C.

After partial cure, the needles are inspected and needles having coatings that have adhered together are mechanically separated (for example manually) and transferred to a curing tray for final cure. The curing tray is placed in a thermal curing oven for a sufficiently effective period of time at a sufficiently effective temperature to fully cure the coatings. The term "fully cure" is defined to mean that the silicone coating is fully cross-linked and has a maximum strength. Typically, the full cure time will be about 10 minutes to about 8 hours, more typically about 30 minutes to about 4 hours, and preferably about 1 hour to about 3 hours. Typically, the full cure temperature is maintained at about 140° C. to about 210° C., more typically about 150° C. to about 195° C., and preferably about 160° C. to about 170° C.

It will be appreciated that although the preferred method of applying the silicone coatings to the needles is a dip process in a coating bath, other alternative coating processes may be utilized to apply the coatings including brushing and spraying. After the coatings are applied to a batch of needles using one of the alternative processes, the needles are cured in accordance with the curing steps of the processes of the present invention.

The silicone coatings produced on medical devices using the novel batch processes of the present invention are superior to and have many advantages over coatings produced in conventional processes. The advantages include improved coating integrity, improved needle performance, and the reduction of visual defects resulting from coating damage.

Figure 2:
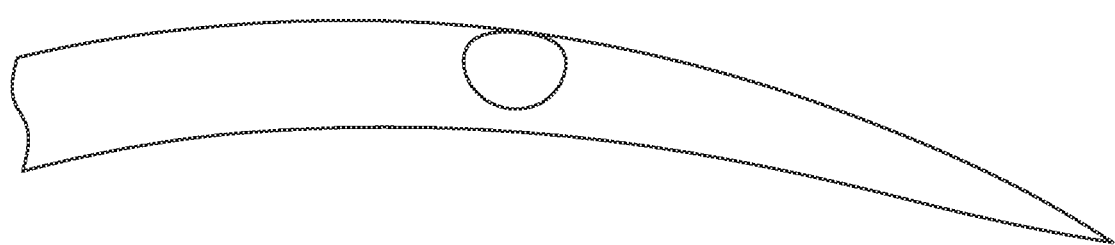
FIG. 2 is a photograph of a cross-linked silicone coating on a needle from a batch after the large batch of needles was partially cured at 100° C. for one hour. The visible defect was formed by separating a pair of needles that had coating sections stuck together after partial curing.
Figure 3:
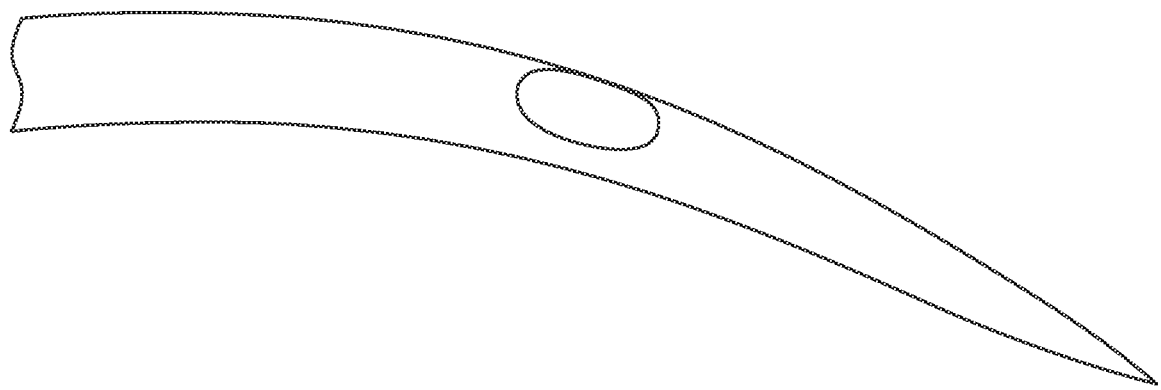
FIG. 3 is a photograph of the same spot of the same needle shown in FIG. 2 after being further heated at 160° C. for one hour resulting in full cure. The defect is seen to be nearly completely repaired or mitigated.

As seen in FIGS. 2-3, surprisingly and unexpectedly, there is observed a self healing of the damaged coatings after the second cure, which is happening, not wishing to be bound by any particular theory, potentially due to a limited re-flow of the partially cured silicone coating during the second cure. This self-curing or self-repair effect makes the process much more efficient, increasing yield, as the needles which would be considered defective can be utilized.

The coating performance of medical devices coated with the novel compositions of the present invention can be tested with a variety of conventional friction or adhesion tests. In the case of surgical needles illustrated in the examples, coating performance, and durability and integrity of the coatings were evaluated using a conventional needle penetration testing device.

The test methods used a testing apparatus to measure the force to penetrate a synthetic substrate representative of soft tissue (Ethicon Curve Needle Tester) or the force to push the needle through the same or similar substrate (body drag). Further details of the test equipment and method can be found in U.S. Pat. No. 5,181,416 and "A synthetic membrane for testing needle penetration". J. of Appl Biomaterials 1993; 4: 157-160, which are incorporated by reference. In the case of the curved needle tester used for surgical needles, coating performance and integrity can be evaluated using the penetration test device.

In utilizing such a needle penetration testing device in the following examples, each coated surgical needle was mounted and held in a mounting fixture on the testing apparatus, such as self-locking tweezers or a similar holding device. The coated needle was then passed by the apparatus through a polymeric medium that was selected to be representative of general human tissue. Approximately half of the needle length was passed through the medium and then retracted prior to the next pass. Further details of the test equipment and method can be found in U.S. Pat. No. 5,181,416. The test media used in the examples was a type of synthetic rubber (Duraflex™, manufactured by Monmouth Rubber and Plastic Corporation, Monmouth, N.J., U.S.A). Each test included using at least 10 needles that were individually passed through the media 30 times each. The maximum force was recorded for each pass and used as a measure of the coating performance. Typically the penetration force increases with each successive pass as the coating wears off from the needle.

The following examples are illustrative of the principles and practice of the present invention, although not limited thereto.

Example 1

Coating Solution Preparation.

A platinum cured, cross-linkable silicone solution was prepared using the components listed in Table 1.

TABLE 1

| Coating Formulation | | |
|---|---|---|
| Component | Trade Name | Weight (g) |
| Trimethylsilyl terminated polydimethysiloxane | Gelest DMS T72 | 96 |
| dimethylvinyl silyl terminated polydimethysiloxane | Gelest DMS V52 | 96 |
| Platinum catalyst 0.02% solution | | 38.4 |
| Trimethylsilyl terminated polymethylhydrosiloxane | Gelest HMS 991 | 1.9 |
| Solvent 1 | Xylene | 407.7 |
| Solvent 2 | Heptane | 2103 |

The coating formulation was prepared in the following manner: 38.4 g of 0.02% Platinum solution was mixed with 407.7 g of xylene for 5 minutes in a conventional mixing vessel at an ambient temperature of about 20-25° C. Then, 96 g of Gelest DMS V52 dimethylvinyl silyl terminated polydimethysiloxane was added to the above mixture and stirred at low speed for 30 minutes. A quantity of 96 g of small pieces of Gelest DMS T-72 trimethylsilyl terminated polydimethysiloxane was added and the mixture was stirred at low speed for 1 hour. Finally, a quantity of 2103 g of heptane was added together with 1.9 g Gelest HMS991 trimethylsilyl terminated polymethylhydrosiloxane and the final mixture was stirred at high speed for one hour.

Example 2

Study on Model Needle to Determine the Partial Curing Temperature.

Seven sets of 10 needles each of uncoated 16 mil Ethicon RB-1 needles (Ethicon, Inc., Somerville, N.J., USA) were dip coated with the cross-linkable silicone solution of Example 1. The coated needles were separated into sets that were heated for 1 hour at 70° C., 90° C., 100° C., 110° C., 120° C. and 140° C., respectively. A separate set of needles was dried at ambient conditions for 24 hours as a baseline sample. Needle penetration testing was used here as an indirect measurement for the coating strength. The results of the first pass penetration of these seven sets of needles are summarized in Table 2. Ten (10) needles were used for each set of needles and the results outlined in Table 2 are the average first pass penetration forces of these 10 needles.

TABLE 2

First Pass Needle Penetration Test: Silicone Coated Needles Cured at Different Temperatures.
16 Mil Needles RB-1 Type

| Curing Temperature (° C.) | Penetration Force (g) |
|---|---|
| Room Temperature (uncured) | 93 |
| 70 | 76 |
| 90 | 60 |
| 100 | 59 |
| 110 | 39 |
| 120 | 35 |
| 140 | 30 |

The data showed that the uncured coating gave the highest penetration forces, while the fully-cured coating gave the lowest penetration forces. The weakness of the uncured coating led to its easy removal from the needle upon initial insertion into the test media, and the needles with the uncured coatings having lost lubrication efficacy very quickly during the penetration process. The fully-cured coating was observed to be strong enough to resist the friction caused by the act of penetration. It was observed in these 7 sets of needles that higher curing temperature led to stronger coatings which are resistant to removal from the needle surface during the interaction with the test media, as indicated by lower first pass penetration forces.

The first pass penetration test results showed that the coating reached a state of a partially cured condition with about half of its strength after heating for 1 hour at a temperature between 90° C. and 100° C.

Example 3

Needles Coated with Cross-Linked Silicone Using a Conventional Batch Coating Procedure.

Figure 4:
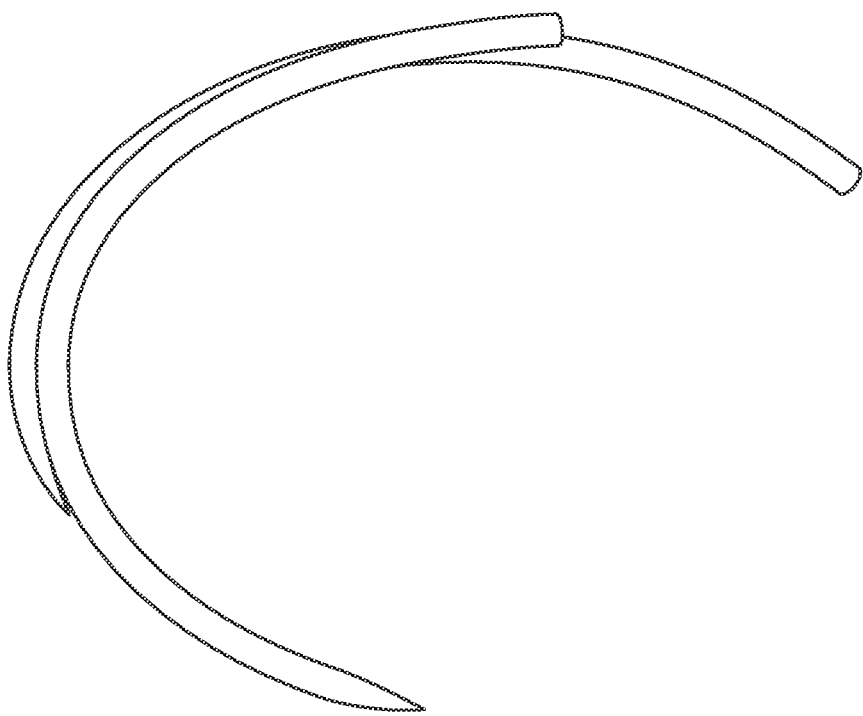
FIG. 4 is a photograph of two cross-linked silicone coated surgical needles having cross-linked silicone coatings that are adhering together at several contact points; the needles were processed in a conventional one-step curing batch process.

180 needles (40 mil Ethicon CT-1) were dipped into the silicone coating solution of Example 1 in a conventional dip tank. The needles were placed into a conventional porous basket. The bath temperature was at ambient temperature. The needles were maintained in the coating bath for about 10 seconds, then the basket with the coated needles was removed from the bath, drained for 30 seconds and the batch of needles was placed onto a conventional drying tray. The coated needles were dried on the tray in a fume hood for 1 hour at ambient conditions. The dried needles were then heated at 160° C. in a conventional convection oven for two hours. Eleven pairs of needles were observed to be stuck together after the heating process, for example see FIG. 4. Thirty (30) of the cured, unpaired needles were submitted for penetration testing, and each of the needles was penetrated 20 times. The average penetration force for each pass is summarized in Table 3a.

TABLE 3a

Needle Penetration Test Results
40 Mil Needle CT-1 Taper Point

| Penetration# | Avg. Force (g) |
|---|---|
| 1 | 123 |
| 10 | 141 |
| 20 | 155 |

Ten (10) of the paired needles were mechanically separated by hand, with some being difficult to separate, and the separation resulting in damage to the coating (see FIG. 1) and also submitted for penetration testing which was conducted as described above, and each of the needles was penetrated 20 times. The average penetration force for each pass is summarized in Table 3b.

TABLE 3b

Needle Penetration Test Results on Paired Needles
40 Mil Needle CT-1 Taper Point

| Penetration# | Avg. Force (g) |
|---|---|
| 1 | 125 |
| 10 | 164 |
| 20 | 191 |

The penetration forces for the separated paired needles were substantially higher than the penetration forces for the unpaired needles in the same batch. The mechanical pair separation process appeared to damage the coatings on the needle surfaces and part of the silicone layer was removed when the needles in a pair were separated from each other.

Example 4

Study on Paired Needles Using Two-Step Curing Process.

The two-step curing process of the present invention was used to minimize the occurrence of paired needles. Batches of 180 needles (40 mil Ethicon CT-1 needles) were initially or partially cured at a series of lower temperatures (listed in Table 2 in Example 2) for one hour. Then, the paired needles were mechanically separated from each other as described in Example 3 and the number of the pairs was recorded. The needles were then subjected to a second cure cycle at a higher temperature (160° C.) to ensure that the coatings on the needles were fully cured. The number of pairs in the batch after the second cure cycle was recorded. Eight temperatures were tested for the first cure cycle with six batches of 180 needles in each batch. The temperatures listed in Table 2 were used for the first step curing cycle for this example and the results are summarized in Table 4.

TABLE 4

Number of Paired Needles After Each Curing Condition

| First Step Curing Temperature (° C.) | Number of Pairs After first cure | Number of Pairs After Second cure (T = 160°) | Total number of pairs after the first cure, mechanical separation, and after the second cure |
|---|---|---|---|
| 70  | 0  | 12 | 12 |
| 80  | 0  | 5  | 5  |
| 90  | 0  | 2  | 2  |
| 100 | 1  | 1  | 2  |
| 110 | 4  | 1  | 5  |
| 120 | 6  | 0  | 6  |
| 140 | 9  | 0  | 9  |
| 160 | 12 | 0  | 12 |

It was observed that lower curing temperatures did not lead to partial curing of the silicone coatings. The number of the paired needles was similar to the needles without a first curing cycle which is outlined in Example 3. It was observed that the high first cure temperature or absence of first cure results in formation of many pairs of needles stuck together which were difficult to separate resulting in lower yields. Further, low first cure temperature also resulted in many pairs of needles stuck together after the second cure. Surprisingly, an intermediate first cure temperature, from about 90° C. to about 100° C. resulted in the formation of a minimal amount of pairs of needles stuck together, and the pairs that have formed are easier to separate resulting in higher yields.

Figure 5:
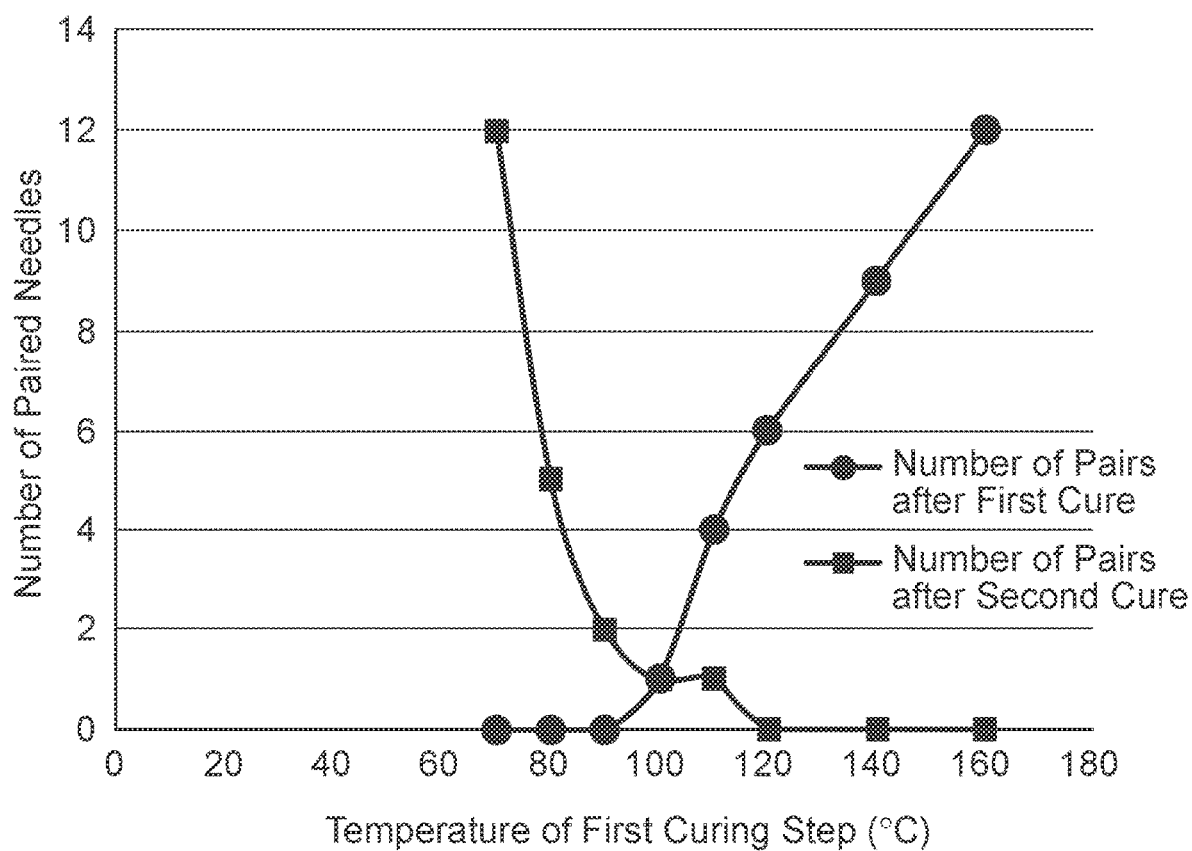
FIG. 5 is a graph showing the number of pairs of cross-linked silicone coated needles that were adhered together; the first curve shows the amount of pairs after the first cure plotted versus the first curing temperature. The second curve shows the amount of pairs after the needles were exposed to first cure, manually separated, and then exposed to the second cure, plotted versus the first curing temperature, with the second curing temperature constant at 160° C. for all tests.
Figure 6:
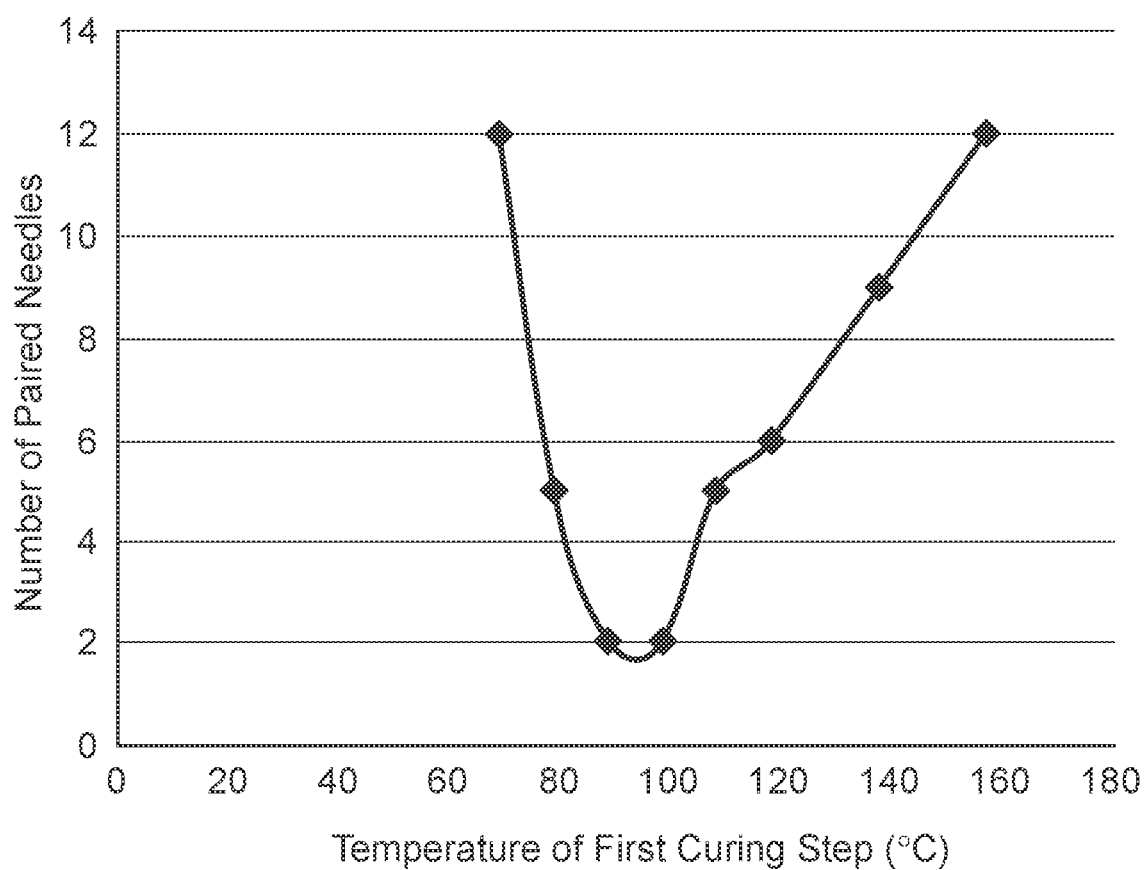
FIG. 6 is a graph showing the combination of the data presented in FIG. 5, with total number of pairs of cross-linked silicone coated needles that were adhered together after first cure and after second cure, plotted versus the first curing temperature, with the second curing temperature constant at 160° C. for all tests.

The data of Table 4 is graphically presented in FIGS. 5 and 6, showing a surprising optimal range of the temperatures for the partial cure being around 90-100° C.

A temperature of 100° C. was selected for the first curing step and Example 5 data as shown below are illustrative of the outcome on the penetration performance of the surgical needles which were made according to the practice of this invention.

Example 5

Needles Cured Using a Two-Step Process 180, 40 mil Ethicon CT-1 needles were dipped into the silicone solution of Example 1 in a dip tank and coated in a manner similar to described in Example 3. The dried needles were heated at 100° C. for one hour for a partial cure in a conventional oven. All of the needles were then separated mechanically separated by hand from each other prior to exposing them to a second curing process at 160° C. for 1 hour resulting in a full cure. Only one pair of needles was observed to be stuck together after the second heating process. Unlike Example 2, unexpectedly the needles in the pairs were easily separated from each other. Thirty (30) of the needles were submitted for penetration test, and each of the needles was penetrated 30 times. The average penetration force for each pass is summarized in Table 5.

TABLE 5

Needle Penetration Test Results
Ethicon 40 Mil Needle CT-1 Taper Point

| Penetration# | Avg. Force (g) |
|---|---|
| 1  | 120 |
| 10 | 136 |
| 20 | 147 |

Example 6

Needles Coated with Condensation Cured Silicone

In a comparative test, 180 Ethicon 40 mil CT-1 needles were dipped into a conventional condensation-cure silicone coating solution consisting of 100 g of Nusil MED 4162 and 900 g of heptane in a dip tank. The coated needles were dried in a fume hood for one hour at ambient conditions. The dried needles were cured by heating in an oven at 160° C. for two hours. Typically a large batch should be cured for a longer time, up to 10 or 24 hours. No needles were observed to be stuck together after the heating process. 30 of the needles were submitted for penetration testing, and each of the needles was penetrated 30 times. The average penetration force for each pass is summarized in Table 6.

TABLE 6

Needle Penetration Test Test Results
Ethicon 40 Mil Needle CT-1 Taper Point

| Penetration# | Avg. Force (g) |
|---|---|
| 1  | 137 |
| 10 | 212 |
| 20 | 246 |

The cross-linked silicone coated needles of Example 5 were observed to give substantially lower penetration forces, especially in $10^{th}$ and $20^{th}$ pass, compared to conventional batch coated needles of the present example, condensation cured silicone (up to 40% reduction in penetration force on $20^{th}$ pass). The novel two-step curing processes of the present invention substantially eliminated the needles stickiness caused by the cross-linked silicone coating and provided coated needles with superior coatings and performance.

Although this invention has been shown and described with respect to detailed embodiments thereof, it will be understood by those skilled in the art that various changes in form and detail thereof may be made without departing from the spirit and scope of the claimed invention.

I claim:

1. A method of batch coating a plurality of surgical needles, comprising:
   providing a plurality of surgical needles, wherein at least some of the needles are in contact with each other;
   then, immersing the needles in a bath containing a silicone coating solution, said solution comprising a cross-linkable siloxane polymer, a non-cross-linkable siloxane polymer, a cross-linking agent, a platinum catalyst, and a solvent to provide a coating on each needle;
   next, removing the needles from the bath;
   then, partially curing the coatings on the needles at a partial cure temperature for a first time period such that the coatings are partially cured, wherein the partial cure temperature is about 90° C. to about 100° C.;

then, mechanically separating the needles; and finally, fully curing the coatings on the needles at a full cure temperature for a second time period such that the coatings are fully cured, the full cure temperature being higher than the partial cure temperature, wherein damage to the coatings after mechanically separating the needles is substantially repaired or mitigated by a limited re-flow of the partially cured coatings during the second time period.

2. The method of claim 1, wherein the needles are placed in a porous containment vessel prior to immersing the needles in the coating bath, and the needles and the vessel are both immersed in the coating bath.

3. The method of claim 1, wherein the silicone coating comprises vinyl terminated polydimethyldisiloxane; methyl terminated polydimethyldisiloxane;
polymethylhydro siloxane; and a platinum catalyst comprising platinum divinyltetramethyldisiloxane ethynylcyclohexanol complex.

4. The method of claim 1, comprising the additional step of removing substantially all of the solvent from the coating prior to the partial curing step.

5. The method of claim 1, wherein the second temperature is at least about 120° C.

6. The method of claim 1, wherein the time for the partial cure is at least about one hour and the time for the second full cure is at least one hour.

7. The method of claim 1, further comprising the step of placing the needles on a dying tray after removing the needles from the coating bath.

8. The method of claim 1, wherein the first and second curing steps are done in an oven.

9. The method of claim 1, wherein the cross-linkable siloxane is selected from the group consisting of dimethylvinylsilyl-terminated polydimethyl siloxane, polydiphenylsilane-dimethylsiloxane copolymer, polyphenylmethylsiloxane, polyfluoropropylmethyl-dimethylsiloxane copolymer and polydiethylsiloxane.

10. The method of claim 1, wherein the non-cross-linkable siloxane is selected from the group consisting of trimethylsilyl-terminated polydimethyl siloxane, polyalkylmethylsiloxane, polydiethylsiloxane, polyfluoropropylmethylsiloxane, polyoctylmethylsiloxane, polytetradecylmethylsiloxane, polyoctadecylmethylsiloxane, polyalkylmethyl dimethylsiloxane, and polyhexadecymethylsiloxane-dimethyl siloxane.

11. The method of claim 1, wherein the cross-linking agent is selected from the group consisting of polymethylhydrosiloxane, polymethylhydro-co-polydimethylsiloxane, polyethyhydrosiloxane, polymethylhydrosiloxane-co-octylmethylsiloxane, and polymethylhydrosiloxane-co-methylphenylsiloxane.

12. The method of claim 1, wherein the catalyst is the Ashby-Karstedt catalyst.

13. The method of claim 1, wherein the catalyst comprises a platinum complex catalyst (platinum vinyltetramethyldisiloxane ethynylcyclohexanol complex) having the formula:

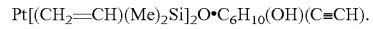

* * * * *